United States Patent [19]

Smith

[11] Patent Number: 4,957,368

[45] Date of Patent: Sep. 18, 1990

[54] APPARATUS AND PROCESS FOR PERFORMING ELLIPSOMETRIC MEASUREMENTS OF SURFACES

[75] Inventor: Tennyson Smith, Orem, Utah

[73] Assignee: Photoacoustic Technology, Inc., Westlake Village, Calif.

[21] Appl. No.: 324,449

[22] Filed: Mar. 16, 1989

[51] Int. Cl.$^5$ .............................................. G01J 4/00
[52] U.S. Cl. ...................................... 356/369; 356/364
[58] Field of Search ............... 356/364, 365, 369, 370, 356/372, 381, 445, 446, 448; 250/225, 578

[56] References Cited

U.S. PATENT DOCUMENTS

| | | | |
|---|---|---|---|
| 3,819,948 | 6/1974 | Lijima et al. | 356/364 |
| 3,880,524 | 4/1975 | Dill et al. | 356/369 |
| 4,381,151 | 4/1983 | Smith | 356/369 |
| 4,750,140 | 6/1988 | Asano et al. | 356/445 |
| 4,837,603 | 6/1989 | Hayashi | 356/369 |

OTHER PUBLICATIONS

Ellipsometry with Pulsed Tunable Laser Source IBM, Technical Disclosure Bulletin, vol. 19, No. 4, Sep. 1976.
Tennyson Smith, "An Automated Scanning Elipsometer" Surface Science, vol. 56 (1976), pp. 212–220.

Primary Examiner—Richard A. Rosenberger
Assistant Examiner—Hoa Pham
Attorney, Agent, or Firm—Gregory O. Garmong

[57] ABSTRACT

A compact ellipsometric apparatus is constructed using as a building block a tri-beam ellipsometric sensor having a monochromatic source of polarized light with a diverging beam of sufficient divergence that three analyzers and associated light detectors may be placed into the beam side by side so that they each receive light reflected from a surface under study at the same angle of reflection. Pairs of these sensors are used together, with one of each pair having in the optical path a quarter wave plate matched to the monochromatic light wavelength and the other of the pair having no quarter wave plate, but with the light wavelength and angle of incidence being the same for each pair. A variety of measurements are made by constructing apparatus using one or more pairs of these basic sensors, the pairs of sensors varying from each other in the light wavelength of the source and the angle of incidence of the polarized beam of light to the surface. Various apparatus having from one to six pairs of sensors have been designed, with higher numbers of sensors providing greater generality in respect to the properties that can be measured.

16 Claims, 5 Drawing Sheets

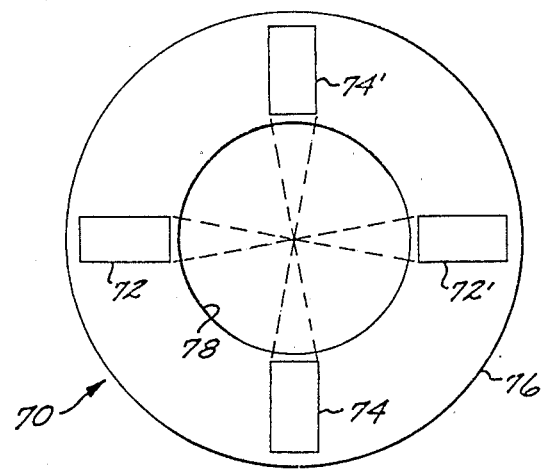
FIG. 4
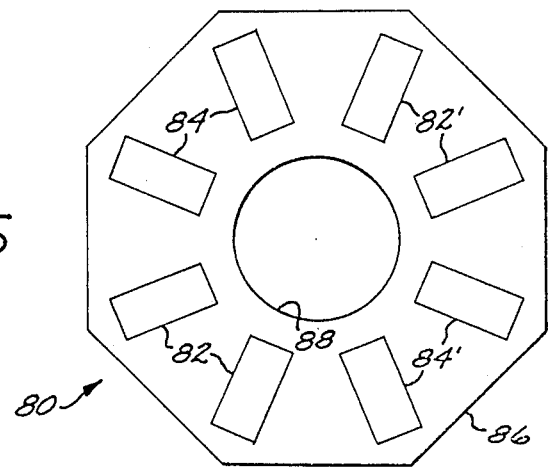
FIG. 5
FIG. 6
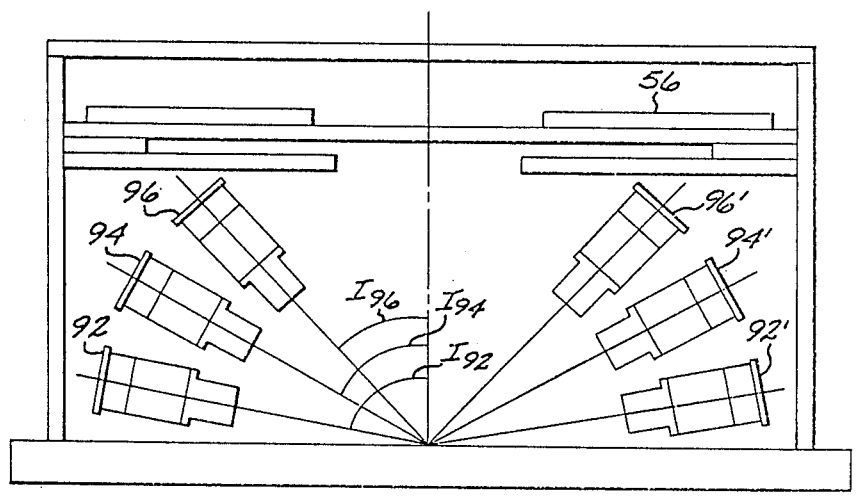

APPARATUS AND PROCESS FOR PERFORMING ELLIPSOMETRIC MEASUREMENTS OF SURFACES

BACKGROUND OF THE INVENTION

This invention relates to the measurement of surface properties of materials, and, more particularly, to the ellipsometric measurement of surface conditions and films on surfaces.

The quality and condition of its surfaces often determine the suitability of a material for use in an industrial process. To cite some examples, if a material is to be painted or bonded to another material, the presence, type, and amount of contaminants such as grease or dirt often determine the success of the painting or bonding operation. Coatings or oxides are placed onto the surface of semiconductor wafers during the fabrication of microelectronic components, and the thickness of the coating or oxide must be established within critical limits for subsequent operations to be successful. The cleanliness of memory disk drive heads must be checked periodically to be certain that contamination does not interfere with read/write functions. These examples are illustrative and not limiting, as there are literally thousands of examples where surface properties are determinative of the operability of the material in its intended use.

In recognition of the critical importance of surfaces, a number of techniques have been developed to observe and measure surface characteristics. Surfaces may be viewed either directly or with magnification. They may be measured by devices such as profilometers which give a quantitative measurement of roughness. In the last 20 years, sophisticated techniques such as Low Energy Electron Diffraction (LEED), Auger Electron Spectroscopy (AES), Scanning Electron Microscopy (SEM), and standard Ellipsometry have been employed for characterizing surfaces, almost always in a laboratory environment.

However, when considered for use in an industrial environment, all of these techniques have serious drawbacks. Most of the available instruments are bulky and expensive to purchase and maintain in operation and calibration. In many cases, such as LEED, AES, and SEM, the pieces under study must be placed into a high-vacuum chamber, thereby limiting the size of the pieces and the rates at which they may be examined.

The greatest drawback, however, is that most of these techniques are not readily adapted to acceptance testing and real-time testing on an industrial scale by relatively unskilled personnel or under computer control. For example, standard ellipsometry may be used to determine the thickness of an oxide coating formed on a surface of a semiconductor material by a particular heat treatment as heat treatment control parameters are being developed. This technique typically is not practical to check every piece subsequently given the nominally same heat treatment.

Instead, it must be assumed that uncontrolled variables do not enter the process and that each heat treatment is successful in producing the desired surface. This assumption fails where there is some error or malfunction in the production operation, and many pieces may be given a bad treatment before the problem is discovered. The most sophisticated inspection techniques therefore cannot be used for real-time control of a production operation, where measurements of all or a large portion of completed parts are used to check whether the production operation is proceeding properly, or whether some adjustment is required.

Additionally, when utilizing many highly advanced surface characterization techniques it is difficult to know whether the characteristic measured is really important and determinative of acceptability of the surface. That is, measurements may be made of surface characteristics, but one is then faced with the problem of deciding whether that measurement is at all relevant to the planned usage of the material and, if so, what the limits of acceptable variation of the measured characteristic might be in order to ensure success of the subsequent processing.

There has therefore existed a continuing need for various types of surface monitoring apparatus which are sensitive to microscopic surface characteristics, are inexpensive, portable, and compact, do not require that the surface to be studied be placed into a vacuum chamber, and allow the development of acceptability and quality control tests which may be utilized by relatively unskilled personnel or under computer control for testing large surfaces and numbers of parts. In particular, it would be useful to have a surface inspection instrument that can be placed near to, or scanned over, the inspection surface itself. In many existing situations, small samples must be taken from the surface and placed into the instrument for analysis, under the implicit, but often erroneous, assumption that the small sample is truly representative of the entire surface.

Two important responses to this need for sophisticated surface inspection techniques usable in a production environment are disclosed in U.S. Pat. Nos. 4,381,151 and 4,590,376, which describe apparatus and techniques for performing light reflection and secondary photoelectron inspections of surfaces, respectively, that may be used in quality control and related activities. The approach of the '376 patent has achieved considerable commercial success in this regard. Each of these approaches has its limitations, however, and other approaches are needed.

However, the need for even further improved apparatus for performing inspections and analysis in a production environment remains. The present invention fulfills this need, and further provides related advantages.

SUMMARY OF THE INVENTION

The present invention provides an apparatus and a technique for performing ellipsometric measurements of surfaces. The approach of the invention is embodied in compact, lightweight, relatively inexpensive apparatus that may be used for inspection of surfaces in a production environment, or in a laboratory. The apparatus has no moving parts, and is therefore sturdy and reliable. The absence of moving parts also permits its speed of operation to be up to 1000 times faster than comparable conventional ellipsometers, which have the added disadvantage of being about 100 times heavier than the present apparatus. The data taken by the instrument can be readily provided to a computer, which is programmed to recognize acceptable ranges of measured parameters, thereby making the approach ideal for acceptability testing. The combination of light weight and small size, high speed operation, reliability, and amenability to computer data analysis make the apparatus highly suited for automated stationary and scanning examination and qualification testing of surfaces in a production environment. Finally, the apparatus can be constructed in several different, increasingly complex and general forms from a single building block structure, permitting the tailoring of the instrument to the required job.

In accordance with one embodiment of the invention, surface measurement apparatus for determining the properties of a surface comprises a pair of ellipsometric sensors, each of the sensors having a structure including a monochromatic light source disposed so as to emit a devergent light beam along an optical path toward the surface at an angle of incidence during operation of the apparatus, a polarizer through which the beam passes before reflecting from the surface being measured, a first polarizing light analyzer through which a first portion of the reflected beam passes and a first detector to measure the intensity of the first portion after it passes through the first light analyzer, a second polarizing light analyzer through which a second portion of the reflected beam passes and a second detector to measure the intensity of the second portion after it passes through the second light analyzer, and a third polarizing light analyzer through which a third portion of the reflected beam passes and a third detector to measure the intensity of the third portion after it passes through the third light analyzer, wherein the operating wavelength of the light source and the angle of incidence for the two sensors are the same, and wherein one of the sensors further includes a quarter wave plate matched to the wavelength of the monochromatic light source, in the optical path of the beam, and the other of the sensors has no quarter wave plate in the optical path of the beam.

Stated alternatively, surface measurement apparatus for determining the properties of a surface comprises a first ellipsometric sensor having a structure including a monochromatic light source disposed so as to emit a divergent light beam along an optical path toward the surface at an angle of incidence during operation of the apparatus, a polarizer through which the beam passes before reflecting from the surface being measured, a first polarizing light analyzer through which a first portion of the reflected beam passes and a first detector to measure the intensity of the first portion after it passes through the first light analyzer, a second polarizing light analyzer through which a second portion of the reflected beam passes and a second detector to measure the intensity of the second portion after it passes through the second light analyzer, and a third polarizing light analyzer through which a third portion of the reflected beam passes and a third detector to measure the intensity of the third portion after it passes through the third light analyzer; and second ellipsometric sensor having a structure including a monochromatic light source disposed so as to emit a divergent light beam along an optical path toward the surface at an angle of incidence during operation of the apparatus, a polarizer through which the beam passes before reflecting from the surface being measured, a first polarizing light analyzer through which a first portion of the reflected beam passes and a first detector to measure the intensity of the first portion after it passes through the first light analyzer, a second polarizing light analyzer through which a second portion of the reflected beam passes and a second detector to measure the intensity of the second portion after it passes through the second light analyzer, and a third polarizing light analyzer through which a third portion of the reflected beam passes and a third detector to measure the intensity of the third portion after it passes through the third light analyzer, and a quarter wave plate matched to the wavelength of the monochromatic light source, in the optical path of the beam, wherein the operating wavelength of the light source for the first sensor and the second sensor are the same, and the angle of incidence for the first sensor and the second sensor are the same.

More generally, surface measurement apparatus for determining the properties of a surface comprises means for measuring the properties of the surface by an ellipsometric measurement, the means including at least one pair of ellipsometric sensors, the sensors of each pair having no moving parts and operating at the same light wavelength and angle of incidence, the sensors of each pair differing in that one sensor has a quarter wave plate in the optical path and the other sensor has no quarter wave plate in the optical path.

The present ivnention also extends to a process for measuring surfaces using multiple measurements of the surface. In accordance with this aspect of the invention, a process for measuring surface properties of a surface, with an apparatus having no moving parts comprises the steps of furnishing at least one pair of ellipsometric sensors that each measure the ellipsometric parameters del and psi without using any moving parts, each of the pairs of sensors being characterized by its wavelength of monochromatic radiation emitted by a light source in the sensor, and angle of incidence of the monochromatic light beam to the surface being measured, one of each pair of sensors having a quarter wave plate in the optical path and the other sensor of the pair having no quarter wave plate in the optical path; setting the different pairs of ellipsometric sensors to different combinations of wavelength of monochromatic radiation and angle of incidence; measuring the properties of a region of the surface using the pairs of ellipsometric sensors and without changing the surface properties of the region during the period when the two measurements are made; and calculating the surface properties of the measured region from the measured properties.

This approach is suited for measurements of a single location on a surface, or for scanning measurements of multiple locations on a surface. To accomplish such measurements, one set of data is taken at a first location on the surface, and then the sensors are moved to perform measurements at a second location on the surface. The measurements and movements to new locations are repeated as many times as desired. The entire surface of a part can be readily mapped in this manner, to as fine a resolution between measurement locations as is desired. Such mapping procedures are possible with conventional ellipsometers but not practical due to the much longer measurement time required, and are certainly not practical in a production environment.

The preferred approach of the invention utilizes a form of ellipsometric sensor that utilizes no moving parts, and is therefore rugged, compact, and able to gather data rapidly. The sensor has a monochromatic light source that produces a beam which is polarized prior to impinging upon the surface under study. When the sensors are paired together in use, identical sensors are used, except that the optical path of one of the sensors includes a quarter wave plate matched to the light radiation, and the other does not. For the sensor, the light beam must be sufficiently diverging that it is broad enough to permit separate portions to be passed through three separate polarizing analyzers, and thence to three separate photodetectors wherein the light intensities are measured. This sensor is stationary in a support and has no moving parts. Its configuration is determined by two principal characteristics selected for the sensor--the wavelength of the light that is produced by the monochromatic source and the angle of incidence (and thence reflection) of the beam relative to the surface (which determines the positions of the light source and the detectors).

One pair of such ellipsometric sensors can, by itself, gather important data about the surface, and films on the surface. However, such data is in general not complete in the sense that the data does not uniquely define the surface and the film in all respects. For some applications, a single pair of sensors is sufficient, as long as no information on film thickness beyond zeroth order is required and the optical properties of the substrate are not to be measured.

In the basic approach, for example, one pair of sensors is used, one of the sensors with a quarter wave plate and one without a quarter wave plate, and with both sensors operating at the same wavelength and angle of incidence. This structure permits measurements of delta in the 0 to 360 degree range, but does not permit the order of the film to be determined.

In ellipsometry, the unknowns to be determined may include the refractive index and absorption index of the substrate, and the refractive index, absorption index, and thickness of any films that might be present. The number of unknowns that can be determined depends upon the number of independent measurements of delta and psi that are measured. Hence, the more independent measurements that can be practically made, the more unambiguous the information that can be obtained.

More generally, therefore, multiple pairs of sensors are used to gather similar types of data, but which may be over larger ranges and be such that a unique definition of the film is possible. When enough data is gathered, the possibility of ambiguity is reduced so that the properties of the film become uniquely defined. Thus, two pairs of sensors are used with one of each pair having a quarter wave plate and the other having no quarter wave plate. In each pair, the two sensors use the same wavelength of light and angle of incidence, but these two conditions are different between the sensors of the two pairs. (As used herein, pairs of sensors are characterized as operating at a different combination of wavelength and angle of incidence, meaning that at least one of wavelength and angle of incidence is different as between the pairs, and possibly both are different.) More specifically, in one approach both sensors of the first pair operate at a first wavelength and both sensors of the second pair operate at a second wavelength, but the angle of incidence for both sensors of both pairs is the same. Further certainty can be introduced by providing additional sensor pairs at other angles of incidence.

Each sensor is preferably supported on an annular structure, with the light source and polarizer (and quarter wave plate, if present) on one side of the annulus and positioned so that the light beam is directed downwardly at the angle of incidence into the open center of the annulus. The three analyzers and detectors are on the other side of the annulus, and are positioned to receive the reflected beam. The divergence of the incident beam is selected so that light is uniformly directed toward the surface and thence reflected to the analyzers and detectors.

The mounting of the sensors around the perimeter of the annular support permit the light beams from all of the sensors to be reflected from the same region on the surface, in the center of the annulus, at the same time, or at least sufficiently close together in time that the surface properties do not change. The electronics, such as amplifiers, are readily mounted on the cover of the annular structure.

As the number of sensors increases, the minimum possible annular diameter necessarily increases to physically accommodate the sensors on the annulus, assuming a constant size of sensor. In an operating version of the instrument having no moving parts, for a four sensor embodiment (two pairs) that has a wide range of generality of measurement, the diameter of the annulus is about 5 inches and the height is about 1½ inches. The entire instrument weighs less than 1 pound. By comparison, a single sensor commercial ellipsometer, which has moving parts, weighs over 100 pounds and is about 18 inches long. The tri-beam, multiple ellipsometric sensor apparatus of the invention can be held in the hand of the user, moved from place to place readily, mounted readily on a traversing mechanism, and in general be used in a manufacturing environment. The unit is sealed on the sides and top to prevent interference and is comparatively rugged. Power can be provided by batteries. The unit is readily interfaced to a microcomputer to permit on-site data collection and analysis.

Thus, the approach of the present invention provides an instrument for ellipsometric evaluation of surfaces in a manufacturing or other non-laboratory environment, and which can be used for acceptance testing or similar applications. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 4 is a schematic top view of an apparatus using one pair of sensors of the type illustrated in FIGS. 1 and 2;

FIG. 5 is a schematic top view of an apparatus using two pairs of sensors of the type illustrated in FIGS. 1 and 2;

FIG. 6 is a schematic side view of an apparatus having three sensors at multiple angles of incidence for each sensor location;

DETAILED DESCRIPTION OF THE PREFERRED EMBODIMENTS

Figure 1:
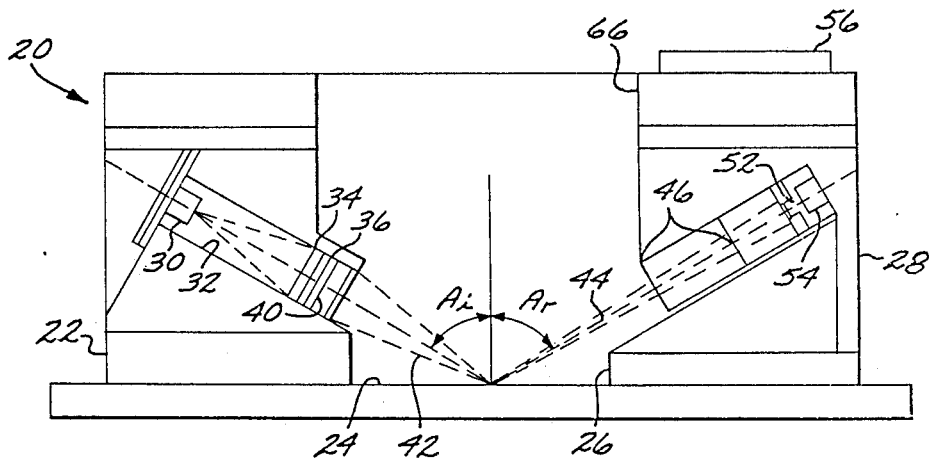
FIG. 1 is a schematic side view of an ellipsometric sensor of the invention.
Figure 2:
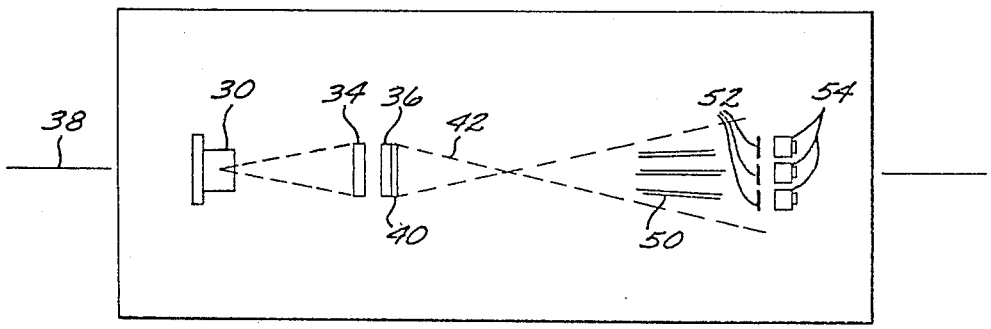
FIG. 2 is a schematic top view of the ellipsometric sensor of FIG. 1, showing only the optical elements.

An ellipsometric sensor 20 is illustrated in FIGS. 1 and 2. The sensor 20 includes a base 22 that is depicted as a flat plate that rests upon the surface 24 being analyzed, but which could be curved as needed to fit the surface if it were curved. The base 22 has an aperture 26 therethrough in the central region of the base. The sensor 20 further includes a housing 28 formed to support the optical elements and electronics of the sensor.

The optical elements of the sensor 20 are mounted to the housing 28. A monochromatic light source 30 is supported from the housing 28 at one end of a collimation bore 32 that permits the light beam emitted by the light source 30 to travel toward the surface 24 along a preselected angle of incidence $A_i$. The light source 30 is preferably a laser or light emitting diode that produces monochromatic light of a preselected wavelength, but could also be a lamp of broad spectrum, whose light is passed through a filter so that only light of the selected wavelength is emitted from the light source. If beam focussing is desired, the light beam passes through a lens system 34 that focuses the beam on the surface 24, so that the beam will be diverging after reflection. The beam then passes through a polarizer 36 that plane polarizes the beam of light with an azimuth of 45 degrees with respect to the plane of incidence 38. (The plane of incidence is the plane of the paper in FIG. 1.)

In one of each pair of the sensors 20, a quarter wave plate 40 is positioned in the beam so that the light beam passes through the quarter wave plate 40. The sensors are otherwise the same in construction.

A polarized beam of light 42 is incident upon the surface 24 in a central region of the aperture 26, at the angle of incidence $A_i$. The beam 42 reflects from the surface 24, primarily at an angle of reflection $A_r$ that is numerically the same as the angle of incidence $A_i$. If needed, the reflected beam 44 passes through collimation slits 46 shown in the side view of FIG. 1, which ensure that only light reflected from the measurement surface 24, of the correct reflection angle $A_r$, strikes the photodetectors. The reflected beam 44 passes through angular collimation slits 46, shown in the side view of FIG. 1, which are set at precisely the correct angle $A_r$ such that only light at this correct angle is passed. Thus, each of three portions 50 of the beam is part of the reflected beam 44 and of the proper angle of reflection $A_r$, and is arranged in a side by side fashion with the other portions 50.

Each of the portions 50 passes through a polarized light analyzer 52, with each portion 50 passing through one and only one of the analyzers 52 (that is, the analyzers are side by side, not one behind the other). One of the analyzers 52 is oriented at an azimuth angle of 0 degrees with respect to the plane of incidence 38, the second of the analyzers 52 is oriented at an azimuth angle of 45 degrees with respect to the plane of incidence 38, and the third of the analyzers 52 is oriented at an azimuth angle of 90 degrees with respect to the plane of incidence 38. Each of the three portions 50 of the reflected beam 44, after passing through the respective analyzer 52, impinges upon a respective photodetector 54. There are three photodetectors 54, one which receives the light passing through the 0 degrees analyzer 52, one which receives the light passing through the 45 degrees analyzer 52, and one which receives the light passing through the 90 degrees analyzer 52. Each photodetector produces a signal that indicates, and is preferably linearly proportional to, the intensity of the respective reflected beam 44 that is impinged upon it.

For the purposes of the subsequent discussion, it is noted that each of the sensors 20 may be characterized by (1) the wavelength of the incident beam of polarized light 42, which is determined by the selection of the source 30, (2) the angle of incidence $A_i$, equal to the angle of reflection $A_r$, which is determined by the geometry of the housing 28 and in the illustrated embodiment by the angle of the collimation bore 32 in which the light source 30 is seated, and (3) the presence or absence of the quarter wave plate 40. The operating pairs of sources 20 are identical as to wavelength and angle of incidence, differing only as to the presence in one of the quarter wave plate and the absence in the other. Another pair of sources might, for example, use light sources 30 of different wavelength and be mounted in the housing at the same angle of incidence. Yet another pair of sources might, for example, have the same wavelength light sources, but be placed in differently angled bores 32 or other mounting arrangement so that the angles of incidence for the two are different. As will be discussed, these several approaches can be used to develop a range of data about the surface from intensity measurements of the three portions 50 for each of the sensors.

Figure 3:
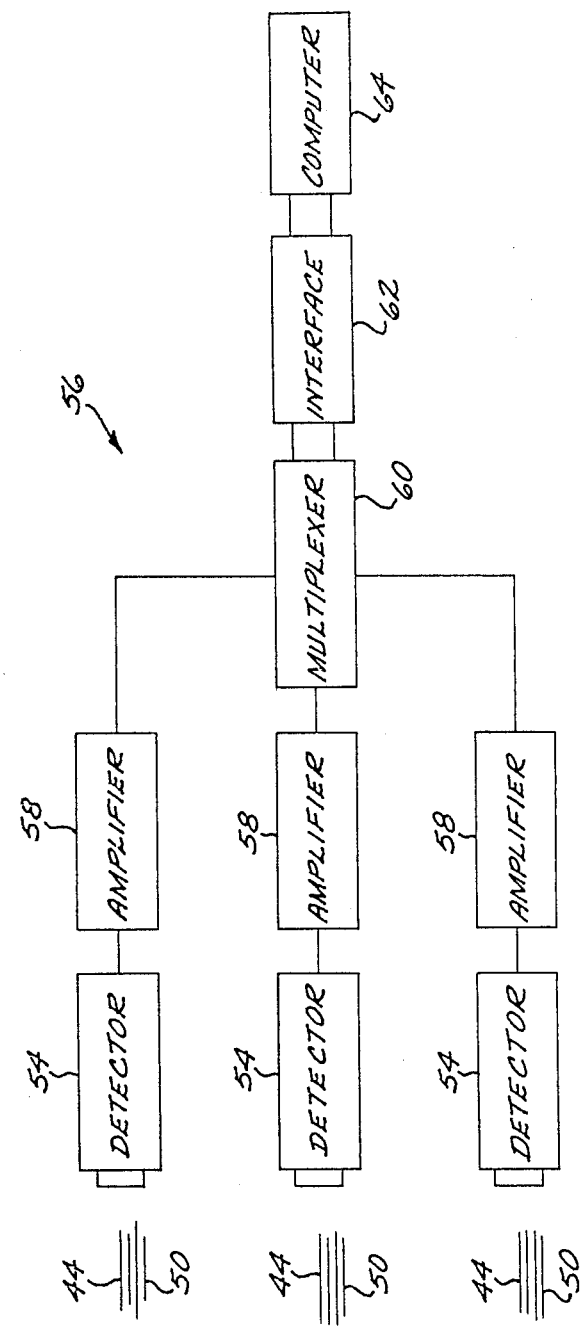
FIG. 3 is a schematic drawing of the control electronics for the sensor of FIGS. 1 and 2.

FIG. 3 illustrates the electronics 56 used for the sensor 20. The electronics 56 include an amplifier 58 for each of the three photodetectors 54 that receive one of the three portions 50 of the reflected beam 44. Each amplifier 58 amplifies the signal received from its associated detector 54. The outputs from the amplifiers 58 are provided to a multiplexer 60 that is controllable to monitor the outputs of the amplifiers 58 either serially or upon command. The selected signal corresponding to a light intensity of one of the photodetectors 54 is sent to a computer interface 62 that includes an analog to digital converter, which digitizes the amplified signal. All of these components 58, 60, and 62 are readily, though not necessarily, provided as part of the electronics 56, and mounted on the housing 28 of the sensor 20. The output signal from the interface 62 is provided to a microprocessor or computer 64, that is usually external to sensor 20.

In some cases the sensor 20 can rest directly upon the surface 24 being measure. Where necessary, it can be spaced from the surface by a mount or supported above the surface, as on a traversing mechanism. The sensor 20 just discussed is small in size, being typically about 3–4 inches in dimension parallel to the surface and about 1 inch in height. The small size is desirable from the standpoint of compactness and portability, and is also desirable in maintaining the reproducibility of the measurements. A small instrument is rigid, and can normally be moved from surface to surface while maintaining operability. If the sensor 20 were very large, movement might result in distortion.

Another feature of the sensor 20 is the aperture 26 and a corresponding central bore 66 that extends downwardly through the instrument to the aperture 26. The surface 24 can be observed either directly or with a microscope through the bore 66 and aperture 26 even while the ellipsometric measurements are made.

In many instances it is desirable to make measurements using more than one sensor at a time, and three embodiments of apparatus for making such measurements are shown in FIGS. 4–6, where the sensors in each case are shown diagrammatically and without the detail previously discussed. In each case, however, the sensor is preferably of the type illustrated in FIGS. 1 and 2, and includes components diametrically opposed across the central bore of the apparatus.

FIG. 4 illustrates an apparatus 70 having one pair of sensors 72 and 74 supported in an annular support 76 having a central bore 78. The two sensors are desirably, but not necessarily, located around the circumference of the annulus 76, as close together circumferentially as possible. The sensor 72 includes two portions 72 and 72', with the light source, lens system, if any, polarizer, and quarter wave plate, if any, located in one portion 72 and the analyzer, collimating slits, and photodetector located in the other portion 72' diametrically opposed across the bore 78. The sensor 74 is similarly structured. In this pair, one sensor 72 has no quarter wave plate, and the other sensor 74 has a quarter wave plate, and the same combination of wavelength of light source and angle of incidence is used for both sensors.

A higher level of complexity and capability is found in the apparatus 80 of FIG. 5, where there are four sensors, which are conveniently discussed as two pairs of sensors. In a first pair of sensors 82, one of the sensors of the pair has a quarter wave plate and the other does not. Both sensors of the first pair 82 are operated at the same light wavelength and angle of incidence of the incident beam. In a second pair of sensors 84, one of the sensors of the pair has a quarter wave plate and the other does not. Both sensors of the second pair 84 are operated at the same light wavelength and angle of incidence. However, the sensors of the second pair 84 do not operate with the same combination of light wavelength and angle of incidence as the two sensors of the first pair 82. That is, either the wavelength, the angle of incidence, or both, of the two sensors of the second pair 84 are different from the corresponding parameters for the first pair 82. The sensors 82 and 84 of the apparatus 80 are mounted around the circumference of an annular support 86, symmetrically at equal angular spacings in the illustration, with the surface being analyzed visible through the central bore 88 of the annulus.

FIG. 6 illustrates an approach for supporting multiple sensors at varying angles of incidence. In the illustrated exemplary embodiment of FIG. 6, three sensors 92, 94, and 96 are mounted at different angles of incidence $I_{92}$, $I_{94}$, and $I_{96}$ relative to the normal to the surface being measured. The sending and receiving portions of the sensors (with and without primes, respectively) are mounted at the same angle to the normal to the surface.

The various approaches for arranging the sensors as shown in FIGS. 4-6 can be readily combined, so that, for example, the apparatus of FIG. 5 could be modified to have three sensors for each angular position, for a total of twelve sensors (six pairs) in the apparatus. In all practical cases, the electronics for the entire apparatus can be readily mounted on the housing in the manner illustrated in FIG. 1. Of course, as the number of sensors increases, normally the diameter and the height of the housing must increase to provide the physical space required to contain the hardware components. Even in the case of 12 sensors, the weight of the apparatus is not more than about 3 pounds.

Figure 7A:
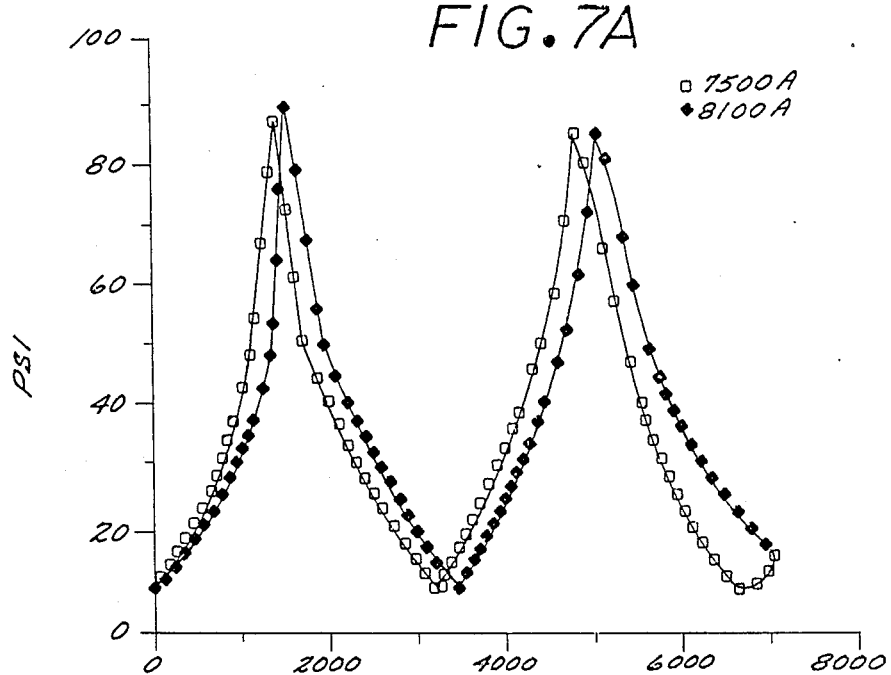
FIG. 7 are graphs of (a) the measured psi and (b) the measured delta values for a film, measured at two different wavelengths of incident radiation.
Figure 7B:
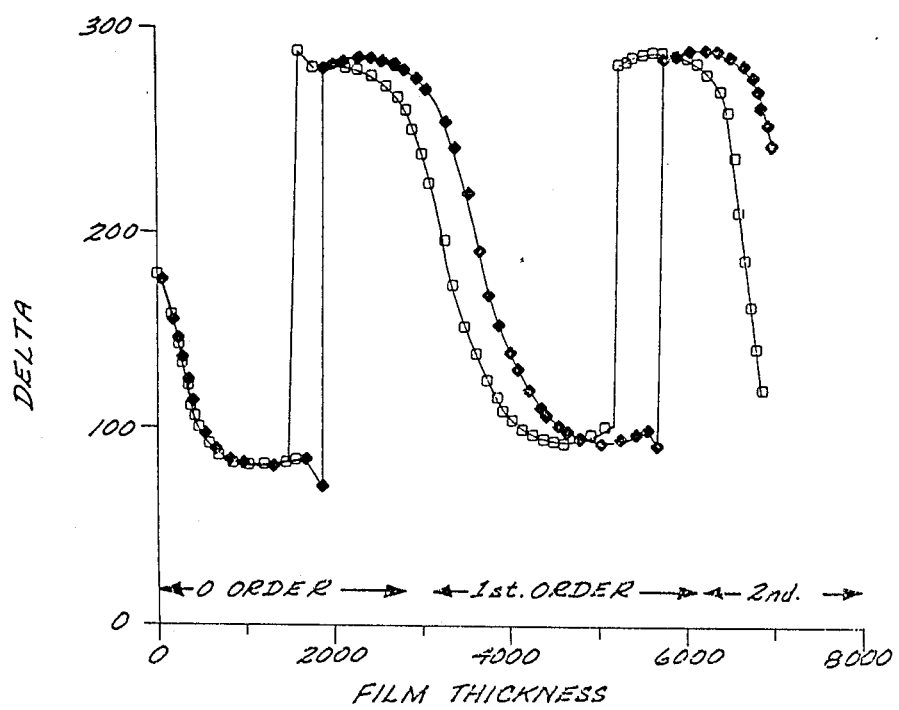

The reason for using more than one sensor is illustrated in FIGS. 7 and 8, which summarize ellipsometric measures of a silicon dioxide film on a silicon substrate, for varying thicknesses of the film. It is not possible to obtain unambiguous data for a film deposited upon a surface from measurements taken with a single wavelength of light or a single angle of incidence. As seen in FIGS. 7(a) and 7(b), for a light wavelength of 7500 Angstroms, the measured values of the ellipsometric parameters delta and psi vary periodically, with a period of about 3300 Angstroms. That is, from a single measurement with a single sensor using light at 7500 Angstroms wavelength, one cannot be certain whether the thickness of the film is X, X+3300 Angstroms, X+6600 Angstroms, etc. However, also as shown in FIGS. 7(a) and 7(b), the repeating period for a different source light wavelength is different, about 3800 Angstroms in the case of light of 8100 Angstroms. The difference in period permits the thickness of the film to be determined from measurements at two source light wavelengths.

Figure 8A:
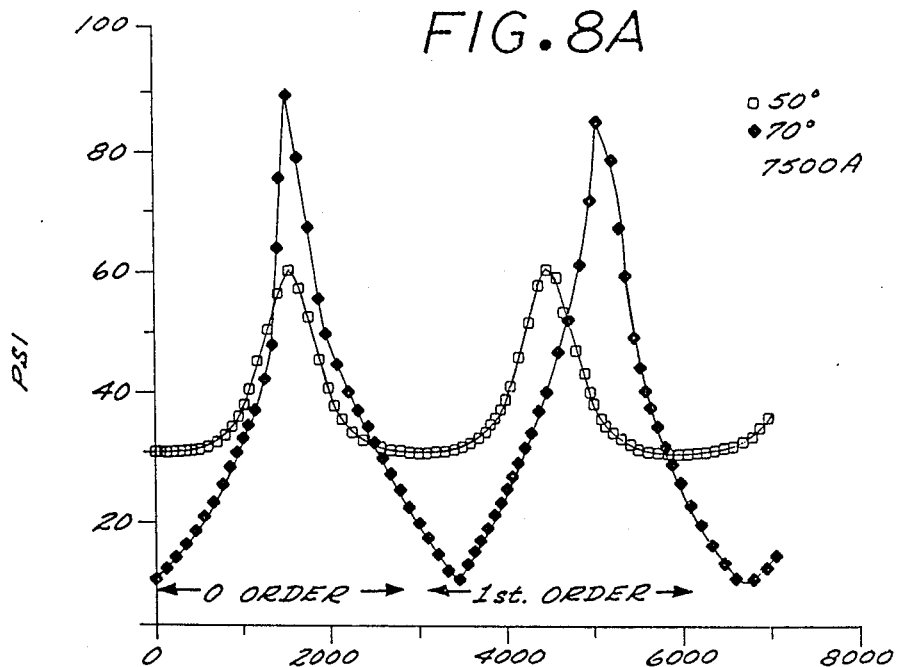
FIG. 8 is a graph of (a) the measured psi and (b) the measured delta values for a film, measured at two different angles of incidence.
Figure 8B:
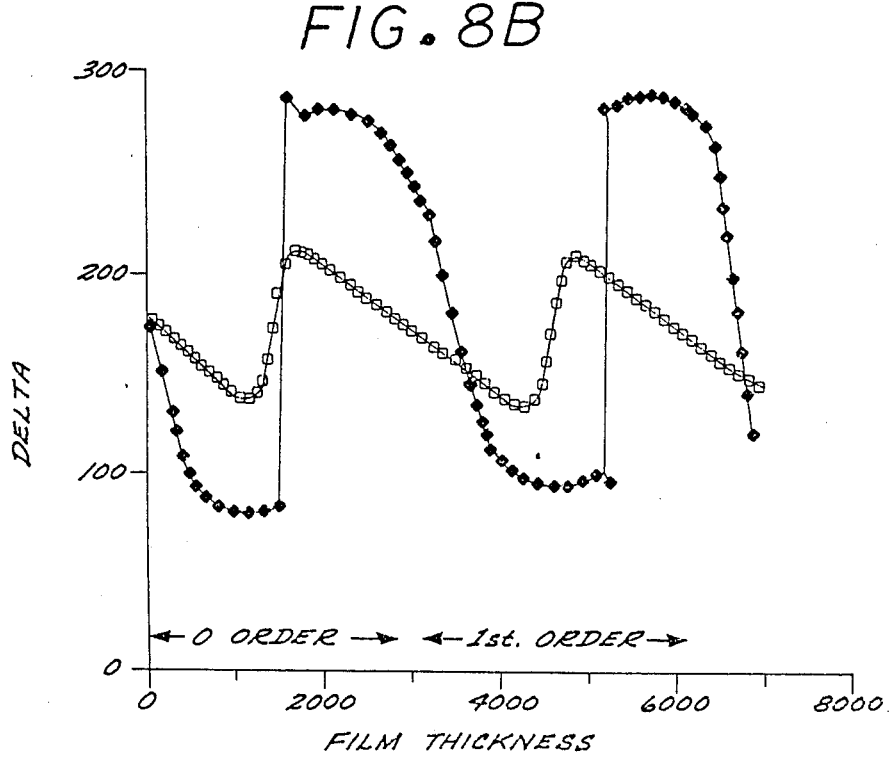

As shown in FIGS. 8(a) and 8(b), there is a similar periodic variation for different angles of incidence, when a single wavelength of incident (7500 Angstroms in FIG. 8) is used. By the judicious selection of different wavelengths and angles of incidence, the delta, psi, and thickness values for a film can be determined unambiguously.

Another complexity is introduced by the approach used to measure the ellipsometric parameter delta (also sometimes termed "del" herein). Delta is determined by measuring its cosine. The arc(cosine) of an angle is restricted to values in the range of 0 degrees to 180 degrees inclusive, so that values in the range of 180 to 360 degrees cannot be measured directly. This problem is circumvented by the use of the quarter wave plate inserted in the optical path. Thus, to make general measurements over the entire range from 0 to 360 degrees, one sensor with no quarter wave plate (0 to 180 degrees) and one sensor with a quarter wave plate (180 to 360 degrees) are used. An alternative approach would be to alternatively insert and withdraw the quarter wave plate from a single sensor, but this approach would be contrary to the objective of avoiding moving parts in the present apparatus.

Thus, in general sensors can be provided with differing source light wavelengths, angles of incidence, and presence or absence of a quarter wave plate in the optical path. However, for some applications such general capability is not required because, for example, it will be known from other sources that the thickness of a film is within a certain thickness range, and it is not necessary to be able to determine which of several periods (or orders) contains the film.

The preferred approach used to calculate the ellipsometric parameters from the measurements of intensity follows that discussed in the publication "An Automated Scanning Ellipsometer" by Tennyson Smith, *Surface Science*, Vol. 56, pages 212-220 (1976). Briefly, the intensities of the reflected light are given by the three equations $$2I^0/I^{45}(i) = R(1 - \cos 2 \cdot \text{psi})$$

$$2I^{90}/I^{45}(i) = R(1 + \cos 2 \cdot \text{psi})$$

$$2I^{45}/I^{45}(i) = R(1 + \sin 2 \cdot \text{psi} \cdot \cos \text{delta})$$

where I with a superscript is the measurable intensity at the analyzer azimuth angle indicated by the superscript, $I^{45}(i)$ is the measured intensity of the incident beam, R is the reflectivity of the surface for the 45 degree polarized incident light, and delta and psi are the ellipsometric parameters. From these equations, a measurement of a calibration specimen with a standard ellipsometer and with the apparatus of the invention, and the measurements of unknown specimens, those skilled in the art can determine the psi and delta parameters used to plot FIGS. 7 and 8. Once these variations are known and part of the computer data base, the film parameters of unknown specimens may be readily determined.

(Although the above-stated mathematical relationships between light intensity and ellipsometric parameters taken from the *Surface Science* article by the present inventor are correct, subsequent to the publication the inventor found that the structural configuration presented there had two shortcomings. First, use of a nondiverging beam made the results too sensitive to sample position and alignment. Second, the absence of a quarter wave plate made it impossible to tell whether the measured delta was in the range of 0 to 180 degrees, or 180 to 360 degrees. The present approach overcomes these problems.)

To check the operation of the tri-beam ellipsometer, an embodiment having two pairs of ellipsometric sensors was constructed. One of each sensors had a quarter wave plate, and the other did not. One pair of sensors was operated with a light source of 7500 Angstroms, and the other pair of sensors was operated with a light source of 8100 Angstroms. All sensors had an angle of incidence of 60 degrees. The device had the annular construction depicted in FIG. 5, was about 5 inches in diameter and 1½ inches in height, and weighed about 1 pound. The following tests were performed using this instrument, on a range of silicon samples that had been oxidized for different times to have silicon dioxide surface layers of different thicknesses.

EXAMPLE 1

The eight samples were measured using the tri-beam ellipsometer of the invention, and for comparison, with a conventional ellipsometer, which weighs over 100 pounds. The columns in Table I provide the measured ellipsometric parameters using the tri-beam ellipsometer, and the measured film thickness, and the final column gives the percentage difference in the value of film thickness measured using the tri-beam ellipsometer as compared with the commerical ellipsometer.

TABLE 1

| No. | Del 7500 | Del 8100 | Psi 7500 | Psi 8100 | Film Thk Angstroms | Pct Diff |
|---|---|---|---|---|---|---|
| 1 | 140 | 144 | 24.8 | 25.2 | 472 | −0.4 |
| 2 | 113 | 119 | 34.7 | 33.7 | 1025 | −0.8 |
| 3 | 194 | 207 | 23.0 | 25.5 | 3091 | 1.7 |
| 4 | 240 | 229 | 32.4 | 56.5 | 5370 | 0.4 |
| 5 | 122 | 125 | 61.3 | 30.8 | 7745 | −0.4 |
| 6 | 235 | 116 | 44.8 | 43.1 | 8194 | −0.9 |
| 7 | 159 | 212 | 23.0 | 26.4 | 9911 | 0.8 |
| 8 | 132 | 127 | 64.1 | 29.1 | 11110 | 0.4 |

The measurements are, in all cases but one, within one percent of each other, suggesting that the tri-beam ellipsometer is accurate within experimental differences. The time for a single measurement using the approach of the invention is about 0.005 seconds, as compared with 5 seconds for the commercial ellipsometer.

EXAMPLE 2

Another sample of silicon oxidized to produce a silicon dioxide film was analyzed in a simulated quality assurance test. A fingerprint was made in one area of the sample, and the other areas were untouched. The apparatus described above and used in Example 1 was used to examine the different areas of the sample. From visual inspection, it could be seen that measurements 1, 2, 3, and 5 were made away from the area of the fingerprint, while measurement 4 was made in the area of the fingerprint.

The measurements indicated the following film thicknesses: Measurement 1, 447 Angstroms; measurement 2, 433 Angstroms; Measurement 3, 426 Angstroms; Measurement 4, 595 Angstroms; Measurement 5, 444 Angstroms. One of the measurements, number 4, had a measured film thickness significantly greater than that established for the other measurements, and, as noted earlier, number 4 was the measurement taken in the visible area of the fingerprint. This information indicates that the presence of fingerprints or other contamination may be detected by the different thickness of surface layer produced by that contamination. This information may therefore be used in an automated quality control system, where the surface is not visually inspected, to detect pieces that have surface contamination that produces a thicker film. For example, all of the values could be averaged and those values greater than a specified deviation from the average indicated as nonconforming and therefore suspect. Except for the fingerprint area, all of the film thicknesses are identical within about 5 percent.

Thus, the present approach provides a fast and versatile method for making measurements of the physical properties of films lying on surfaces. Although particular embodiments of the invention have been described in detail for purposes of illustration, various modifications may be made without departing from the spirit and scope of the invention. Accordingly, the invention is not to be limited except as by the appended claims.

What is claimed is:

1. Surface measurement apparatus for determining the properties of a surface, comprising:

a pair of ellipsometric sensors, each of the sensors having a structure including a monochromatic light source disposed so as to emit a devergent light beam along an optical path toward the surface at an angle of incidence during operation of the apparatus.

a polarizer through which the beam passes before reflecting from the surface being measured, a first polarizing light analyzer through which a first portion of the reflected beam passes and a first detector to measure the intensity of the first portion after it passes through the first light analyzer, a second polarizing light analyzer through which a second portion of the reflected beam passes and a second detector to measure the intensity of the second portion after it passes through the second light analyzer, and a third polarizing light analyzer through which a third portion of the reflected beam passes and a third detector to measure the intensity of the third portion after it passes through the third light analyzer, wherein the operating wavelength of the light source and the angle of incidence for the two sensors are the same, and wherein one of the sensors further includes a quarter wave plate matched to the wavelength of the monochromatic light source, in the optical path of the beam, and the other of the sensors has no quarter wave plate in the optical path of the beam.

2. The apparatus of claim 1, further including a second pair of sensors, the second pair of sensors having the same structure and operation as the first pair of sensors except that the light sources of the second pair of sensors operate at a different wavelength than the light sources of the first pair of sensors.

3. The apparatus of claim 2, further including at least one additional pair of sensors, the additional pairs of sensors having the same structure and operation as the first pair of sensors, except that the additional pairs of sensors operate at a different combination of source wavelength and angle of incidence than either the first or the second pair of sensors.

4. The apparatus of claim 1, further including a second pair of sensors, the second pair of sensors having the same structure and operation as the first pair of sensors except that the angle of incidence of the second pair of sensors is different than the angle of incidence of the first pair of sensors.

5. The apparatus of claim 3, further including at least one additional pair of sensors, the additonal pairs of sensors having the same structure and operation as the first pair of sensors, except that the additional pairs of sensors operate at a different combination of source wavelength and angle of incidence than either the first or the second pair of sensors.

6. The apparatus of claim 1, further including, between the light source and the polarizer of each of the sensors,
a lens set that focuses the beam to the point of reflection from the surface of the surface being studied.

7. The apparatus of claim 1, wherein the light source is a lamp with a filter.

8. The apparatus of claim 1, wherein the light source for each sensor is a light emitting diode.

9. The apparatus of claim 1, further including
collimating slits that limit the dimensions of the portion of the beam incident upon the light detectors and prevent light reflecting from any surface other than the measurement surface from entering the detectors.

10. The apparatus of claim 1, further including
an amplifier connected to the output signal of each of the detectors.

11. Surface measurement apparatus for determining the properties of a surface, comprising:
a first ellipsometric sensor having a structure including
a monochromatic light source disposed so as to emit a divergent light beam along an optical path toward the surface at an angle of incidence during operation of the apparatus,
a polarizer through which the beam passes before reflecting from the surface being measured,
a first polarizing light analyzer through which a first portion of the reflected beam passes and a first detector to measure the intensity of the first portion after it passes through the first light analyzer,
a second polarizing light analyzer through which a second portion of the reflected beam passes and a second detector to measure the intensity of the second portion after it passes through the second light analyzer, and
a third polarizing light analyzer through which a third portion of the reflected beam passes and a third detector to measure the intensity of the third portion after it passes through the third light analyzer; and
a second ellipsometric sensor having a structure including
a monochromatic light source disposed so as to emit a divergent light beam along an optical path toward the surface at an angle of incidence during operation of the apparatus,
a polarizer through which the beam passes before reflecting from the surface being measured,
a first polarizing light analyzer through which a first portion of the reflected beam passes and a first detector to measure the intensity of the first portion after it passes through the first light analyzer,
a second polarizing light analyzer through which a second portion of the reflected beam passes and a second detector to measure the intensity of the second portion after it passes through the second light analyzer, and
a third polarizing light analyzer through which a third portion of the reflected beam passes and a third detector to measure the intensity of the third portion after it passes through the third light analyzer, and
a quarter wave plate matched to the wavelength of the monochromatic light source, in the optical path of the beam, wherein the operating wavelength of the light source for the first sensor and the second sensor are the same, and the angle of incidence for the first sensor and the second sensor are the same.

12. Surface measurement apparatus for determining the properties of a surface, comprising:
means for measuring the properties of the surface by an ellipsometric measurement, the means including at least one pair of ellipsometric sensors, the sensors of each pair having no moving parts and operating at the same light wavelength and angle of incidence, the sensors of each pair differing in that one sensor has a quarter wave plate in the optical path and the other sensor has no quarter wave plate in the optical path.

13. The apparatus of claim 12, wherein the means for measuring includes at least two pairs of ellipsometric sensors, each of which pairs of sensors operates at a different combination of light wavelength and angle of incidence than the other pairs of sensors.

14. A process for measuring surface properties of a surface, with an apparatus having no moving parts, comprising the steps of:
furnishing at least one pair of ellipsometric sensors that each measure the ellipsometric parameters del and psi without using any moving parts, each of the pairs of sensors being characterized by its wavelength of monochromatic radiation emitted by a light source in the sensor, and angle of incidence of the monochromatic light beam of the surface being measured, one of each pair of sensors having a quarter wave plate in the optical path and the other sensor of the pair having no quarter wave plate in the optical path;
setting the different pairs of ellipsometric sensors to different combinations of wavelength of monochromatic radiation and angle of incidence;
measuring the properties of a region of the surface using the pairs of ellipsometric sensors and without changing the surface properties of the region during the period when the two measurements are made; and
calculating the surface properties of the measured region from the measured properties.

15. The process of claim 14, wherein the two sensors, supplied in the step of furnishing, utilize light sources with divergent beams.

16. The process of claim 14, including the additional step of:
moving the apparatus relative to the surface to a second surface location, and repeating the steps of setting, measuring, and calculating at the second surface location.

* * * * *